United States Patent [19]

Lormeau et al.

[11] Patent Number: 5,891,647
[45] Date of Patent: Apr. 6, 1999

[54] METHOD FOR THE IMMUNOASSAY OF ANTITHROMBIN III ACTIVATED BY A GLYCOSAMINOGLYCAN, CORRESPONDING MONOCLONAL ANTIBODIES AND METHOD FOR OBTAINING THEM

[75] Inventors: Jean-Claude Lormeau, Kremlin Bicetre; Renee Georgette Milleblandine, Perpignan; Francis Egiste Joseph Paolucci; Bernard Pau, both of Montpellier, all of France

[73] Assignee: Pasteur Sanofi Diagnostics, Marnes la Coquette, France

[21] Appl. No.: 727,427

[22] PCT Filed: Apr. 10, 1995

[86] PCT No.: PCT/FR95/00456

§ 371 Date: Oct. 11, 1996

§ 102(e) Date: Oct. 11, 1996

[87] PCT Pub. No.: WO95/28644

PCT Pub. Date: Oct. 26, 1995

[30] Foreign Application Priority Data

Apr. 14, 1994 [FR] France ................................. 94 04469

[51] Int. Cl.⁶ ........................ G01N 33/53; G01N 33/543; C12P 21/06; C07K 16/00
[52] U.S. Cl. ........................ 435/7.2; 435/70.21; 436/518; 436/519; 530/387.1; 530/388.25
[58] Field of Search ................................. 435/7.2, 70.21; 436/519, 518; 530/388.25, 387.1

[56] References Cited

FOREIGN PATENT DOCUMENTS

| 0896543 | 8/1983 | Belgium . |
|---|---|---|
| 0 165 134 | 5/1985 | European Pat. Off. . |
| 0341927A1 | 5/1989 | European Pat. Off. . |
| 94 153810 | 4/1994 | European Pat. Off. . |
| 2535306 | 5/1984 | France . |
| 2 645 647 | 4/1990 | France . |
| 27 08 985 | 9/1977 | Germany . |
| 28 045 90 | 2/1988 | Germany . |

OTHER PUBLICATIONS

J. Dawes et al., "Biochemistry", Apr. 12, 1994, vol. 33, No. 14, pp. 4375–4383, Easton US.

S. Knoller et al., European Journal of Biochemistry, Feb. 1989, vol. 180, No. 2, pp. 319–326, Berlin de.

Search report (France) for corresponding application.

Translation (English) of international preliminary examination report.

Hrkal, Z. et al, Hybridoma, 10(5):633–640, 1991.

Olds, R.J. et al, Blood, 79(5):1206–1212, Mar. 1, 1992.

Wisdom, Brian, Clin. Chem, 22(8):1243–1255, 1976.

Primary Examiner—James C. Housel
Assistant Examiner—S. Devi
Attorney, Agent, or Firm—Jacobson, Price, Holman & Stern, PLLC

[57] ABSTRACT

A method that assays activated antithrombin III (AT III) is useful for monitoring the effect in vivo of an agent that activates AT III. It involves the steps of contacting AT III with a solution sample containing the agent, wherein the agent is a sulfated glycosaminoglycan or a sulfated oligosaccharide, followed by contacting the sample with i) a first monoclonal antibody that preferentially binds AT III activated by the agent, as opposed to binding native AT III, and ii) a second monoclonal antibody that preferentially binds denatured AT III as opposed to either AT III activated by the agent or native AT III.

22 Claims, 4 Drawing Sheets

METHOD FOR THE IMMUNOASSAY OF ANTITHROMBIN III ACTIVATED BY A GLYCOSAMINOGLYCAN, CORRESPONDING MONOCLONAL ANTIBODIES AND METHOD FOR OBTAINING THEM

This application is filed as a 371 of the international patent application PCT/FR95/00456 filed 10 Apr. 1995.

The present invention relates to an immunological method for the assay of antithrombin III (AT III) activated by one of the sulphated glycosaminoglycans which are known to act on the process of blood coagulation at AT III level. In the presence of heparin, AT III exerts its anticoagulant activity by inhibiting various serum proteases involved in the reactions leading to the formation of insoluble fibrin, especially thrombin and factor Xa.

Various biochemical analogue glycosaminoglycans are known which, on binding to AT III, interrupt the succession of enzyme reactions ending in the clot; natural porcine or bovine heparins and low molecular weight heparins, several types of which are on the market, may be mentioned in particular. Some sulphated oligosaccharides having the same properties are also known, including those described in Patent Applications EP-A-84,999, EP-A-133,599 and EP-A-356,275, in particular the pentasaccharide recognized as constituting the sequence of the heparin chains to which AT III binds.

These compounds may be used in man as anticoagulants and antithrombotics in prophylactic or therapeutic treatments; however, monitoring of the state of the coagulation system during these treatments is essential given their potential side-effects, and in particular their risks of haemorrhage which vary from individual to individual.

Monitoring is currently based on biological methods which consist in determining in vitro the inhibitory action at factor Xa level of the sulphated glycosaminoglycans present in the patient's blood, either by a specific coagulation test for this factor, or by measuring its residual activity on a chromogenic substrate. For a description of these tests, reference may be made to the work: l'héparine [heparin]—J. P. Duclos—Editions Masson (1984).

In man, the efficacious blood concentrations of antithrombotic glycosaminoglycans are low, less than 10 $\mu$M, and in the absence of specific antibodies, no direct assay of these products which can be used routinely in biological analytical laboratories has been developed.

However, it should be noted that the results obtained with the above two methods are sometimes divergent and poorly correlated with the antithrombotic activity observed in vivo and with the extent of the risks of haemorrhage, as mentioned by A. Leizorovicz, L. Bara, M. M. Samama and M. C. Haugh dans Haemostasis (1993), 23, (sup. 1), pp. 89–98. In addition, they do not always reflect the clinical situation and, in particular, they underestimate high levels of heparin and of similar glycosaminoglycans.

It was hence desirable to have at one's disposal a simple and reliable method enabling the extent of the action of one of these sulphated glycosaminoglycans on plasma AT III in the coagulation cascade to be assessed. It is known that this action, during which heparin or its analogues bind transiently to AT III, manifests itself in particular by a conformational modification of the protein which is the source of the increase in the rate of inhibition of factor Xa.

A determination of the proportion, probably low, of AT III in this activated state, that is to say in a form modified by the binding of heparin or of glycosaminoglycans, which precedes the covalent binding of AT III to the other proteabes of coagulation, should enable the intensity of the inhibitory action of the sulphated glycosaminoglycan present in the plasma to be assessed better than by the previous biological methods.

Monoclonal antibodies are known to be very suitable for the identification and determination of specific spatial conformations.

Application JP 6094713 describes a method for the assay of AT III activity by affinity chromatography.

According to this method, the determination of heparin-AT III complexes employs only a single type of labelled antibody specific for these complexes. Moreover, Application DE-2,708,985 describes a method for the evaluation of plasma heparin levels, according to which the amount of AT III complexed with heparin is measured using antibodies specific for the AT III-thrombin complex. A method for the immunoassay of AT III-protease complexes, employing the use of antibodies or antibody fragments specifically binding AT III complexed with a serine esterase but not reacting with free AT III, is described in Application FR-2,645,647. Diagnostic probes for the assay of AT III modified by elastase are described in Application DE-3804590. This document reports antibodies capable of recognizing denatured AT III and not native AT III.

The present invention relates to an immunoassay method of the sandwich type, also known as extraction-saturation type, for the determination of anti-thrombin III activated by a sulphated glycosaminoglycan, employing a pair of monoclonal antibodies which, in combination, recognize AT III activated by one of these sulphated glycosaminoglycans more effectively than native AT III or denatured AT III. One of these antibodies recognizes, in solution, native AT III less effectively than AT III activated by one of the sulphated glycosaminoglycans; the other hardly recognizes, in solution, native or activated AT III but recognizes denatured AT III.

Native AT III is understood to mean AT III, purified or otherwise, in solution in a buffer or in a plasma, where appropriate diluted.

AT III activated by an antithrombotic sulphated glycosaminoglycan is understood to mean AT III in solution in a buffer or in a plasma, where appropriate diluted, in which the glycosaminoglycan is also present, at relative concentrations compatible with their biological activities. Normally, the plasma AT III concentration is in the region of 2.7 $\mu$M; it is lower in some hereditary or acquired pathological states. The maximum tolerable plasma concentrations of the antithrombotic sulphated glycosaminoglycans are dependent on their intrinsic activities and their toxicity. It is known, for example, that, for heparin, the peak plasma concentration is approximately 0.4 $\mu$M, while for low molecular weight heparins it can reach 2 $\mu$M; for the pentasaccharide A of formula:

described in Thromb. Res. (1986), 43, pp. 243–248, the concentration will be of the order of 1 μM.

Denatured AT III is understood to mean AT III treated with guanidine or one of its salts as described by J. Watton et al. in Biochem, (1993), 32, pp. 6501–6505, such that its conformation at the binding site of AT III for heparin and at that for the protease which it inhibits are modified.

Another example of denatured AT III is AT III adsorbed on the surface of a polymer, for example on that of the wells of a microtitration plate, or of microbeads, made of polystyrene or of polyvinyl chloride, which are commonly used in immunodiagnosis.

Throughout the text, AT III is understood to mean human antithrombin III or that of the animal species in which the immunoassay according to the invention is performed.

The monoclonal antibodies needed for carrying out the immunoassay method are also a subject of the invention.

Monoclonal antibodies directed against epitopes of antithrombin III have already been described, in particular, in Eur. J. Biochem, (1989), 180, pp. 319–326; Blood Coagulation Fibrinolysis, (1990), 1, pp. 619–626; or Hybridoma, (1991), 10, pp. 633–640. Their binding to the covalent antithrombin III-thrombin complex or to antithrombin III in the presence of heparin has sometimes been studied, but it has not yet been mentioned or suggested that monoclonal antibodies might attach themselves to AT III activated by the binding of heparin, or of similar sulphated glycosaminoglycans, better than to native AT III.

The obtaining of a monoclonal antibody specific for AT III complexed with heparin, which is useful for studying the conformational changes of AT III in relation to its inhibitory effect on thrombin, is also described in Biochemistry (1994), 33 (14), pp. 4375–4383.

This antibody was prepared from a covalent AT-heparin complex, and does not distinguish between native AT III and AT III activated by a sulphated glycosaminoglycan such as heparin.

According to a first aspect, the invention relates to monoclonal antibodies which recognize antithrombin III in solution, the antithrombin being activated by the binding of a sulphated glycosaminoglycan biochemically similar to heparin, and which possibly recognize antithromnbin III in solution in its native state, purified or otherwise, but which then bind preferentially to the activated AT III.

The capacity of the monoclonal antibodies of the invention to recognize activated AT III preferentially may be studied by any means enabling the affinity of the antibody for its antigen to be measured or assessed. It is possible, in particular, to use an apparatus which enables the variation of the amount of macromolecules, such as proteins, which are bound directly or otherwise to a glass surface coated with a thin layer of gold to be monitored by measuring the angle of total reflection of a polarized monochromatic light ray at the said surface, a phenomenon known by the name of surface plasmon resonance; this technique is described, in particular, in J. Chromat., (1992), 597, pp. 397–410 and EP-A-341,927.

An apparatus of this type is marketed by the company Pharmacia, Sweden under the brand name BIACORE®, or by Fisons Applied Sensor technology, Great Britain under the name Iasys®. The BIACORE® apparatus is the one which has been used below.

To determine the affinity of an antigen for an antibody, one of the two components of the immunological pair is attached to the surface of the biosensor, while the other is in a solution which flows continuously in contact with the said surface in the measuring cell; the signal is a function of the amount of material binding to the biosensor, which enables the rate of complexing of the antigen and the antibody to be determined. In general, the component "attached" to the surface is attached via an antibody which is bound thereto through a covalent bond.

Inasmuch as the immunological method according to the invention is directed towards studying AT III in the presence of sulphated glycosaminoglycan in solution, the antibody under study is the component which will be bound to the sensitive surface, for example as recommended by the manufacturer, via an antibody to immunoglobulins of the species of the antibody studied, while the antigen will be introduced into the flowing solution, which may be the plasma of a normal subject, where appropriate diluted, or a buffer solution; the concentration of the antigen therein will be dependent on the specific characteristics of the apparatus, and in particular on the amount of antibody attached to the sensitive surface. In tests in the presence of heparin and similar glycosaminoglycans, the ratio of the concentrations of these compounds to AT III will be of the order of 1 to 100 times the maximum ratio which may be found in vivo; it is known, in effect, that activated AT III is in the presence of a proportion of AT III remaining free, and it is important to shift the equilibrium towards activated AT III using a marked excess of heparin-like activator in order to be able to make a significant measurement with this BIACORE® apparatus.

It is also possible to determine the relative affinities of a monoclonal antibody for AT III and activated AT III by comparing it in the method of the invention with a known monoclonal antibody corresponding to the invention.

According to a second aspect, the invention relates to monoclonal antibodies which hardly recognize native AT III and AT III activated by glycosaminoglycans biologically similar to heparin, but which recognize denatured AT III. The absence of affinity of this second type of monoclonal antibody with respect to native or activated AT III may also be studied with an apparatus similar to the one mentioned above, on the understanding that the antibody will be considered hardly to recognize activated or native AT III when the signal measured with the BIACORE® is more than two or three times smaller than that measured with the other types of antibody.

The affinity for AT III denatured, in particular, by treatment with guanidine chloride may also be studied with an apparatus for the determination of immunological affinities, but also, more simply, by a conventional immunoassay, for example a solid-phase immunoassay in which the AT III will be immobilized by adsorption, and the monoclonal antibody under study, which would be immunologically bound to the adsorbed AT III after incubation, will be visualized, for example with a conventionally labelled anti-mouse immunoglobulin antibody; preferably, the antibody under study will be immobilized, and the denatured AT III, which would be immunologically bound thereto after incubation, will be visualized with a labelled anti-AT III polyclonal antibody; under the same conditions, native AT III should hardly be recognized.

Among the monoclonal antibodies of the invention that do not recognize either activated AT III or native AT III but recognize denatured AT III, the antibody secreted by the hybridoma deposited on 18th Mar. 1994, in accordance with the Budapest Treaty, at the German Microorganism Collection DSM, D-3300 Braunschwig, Germany under the number ACC 2167 is especially preferred. This hybridoma is another subject of the invention, as are those which secrete the different types of monoclonal antibodies according to the invention.

Moreover, any monoclonal antibody which, when it is paired with monoclonal antibodies that recognize activated AT III, enables the latter antibodies to recognize activated AT III more effectively than native AT III also forms part of this invention.

According to another of its aspects, the invention relates to the method for obtaining these antibodies.

This method consists in performing a lymphocyte hybridization, immunizing animals with human antithrombin III activated by an antithrombotic sulphated oligosaccharide, and then in selecting the hybridomas producing monoclonal antibodies displaying the desired immunological properties, that is to say those which have more affinity for activated AT III in solution than for native AT III, and those which recognize AT III denatured, for example, with guanidine and its salts, in particular guanidine hydrochloride, and hardly recognize native AT III and activated AT III.

The animals, preferably mice, are immunized by a conventional method, by repeated injection, in particular intraperitoneally, of human AT III and then the selected oligosaccharide, or of the mixture of AT III and oligosaccharide. It is not, in general, necessary to repeat the injection of AT III, while a daily injection of oligosaccharide should be performed for 4 to 6 days in order to maintain the AT III in the presence of a high concentration of the oligosaccharide for a certain length of time. A person skilled in the art will adapt the number of injections to the lifetime of the activator. For the immunization, the sulphated oligosaccharides suitable for the activation of AT III will be selected from molecules having 5 to 20 saccharide units, preferably 5 to 10, which are biologically equivalent to heparin and activate AT III, such as the ones described in European Patents EP-84,999, EP-133,599 and EP-356,275, which may be prepared by chemical synthesis.

The pentasaccharide A mentioned above is especially preferred.

The doses of AT III injected must be sufficient to trigger an immune reaction, including a reaction against the activated form, but must not be the source of serious haemorrhages; in general, from 20 $\mu$g to 60 $\mu$g of AT III will be injected for a mouse weighing approximately 25 g.

While a monoclonal antibody to heparin was described recently in Anal. Biochem, (1992), 201, pp. 1–8, which does not recognize an epitope linked to anticoagulant activity, oligosaccharides are not, in general, immunogenic in themselves, so that they may be administered at doses enabling sufficient concentrations to be obtained for a substantial immunological reaction to take place against the activated AT III which has formed in the animal. It is obvious that the injected daily dose of oligosaccharide must also be compatible with the survival of the mice; for the pentasaccharide A, it can be between 10 and 30 $\mu$g per mouse.

For oligosaccharides of longer lifetime, a single injection of the mixture is, in general, sufficient.

The injections may advantageously be repeated after a few days or a few weeks. The immunization protocol is not critical, provided the risks of toxicity, in particular of possible haemorrhages, are taken into account. The method described in Eur. J. Biochem, (1989), 180, pp. 319–326, may be mentioned in particular.

The mice capable of being suitable for lymphocyte hybridization are then selected by looking for the immune serum which displays the strongest immunological reaction with respect to the AT III in solution; it has, in effect, been found that, in such a polyclonal serum, antibodies directed both against native AT III and activated AT III in solution and against denatured AT III are found, and there is no need at this stage to employ more complex selection methods. The affinity of the serum for AT III in solution is determined by a conventional immunometric method, immobilizing the serum under study by adsorption on a plastic surface or via an anti-mouse IgG antibody before an incubation with a solution of native AT III, and then, after washing, bringing a labelled anti-AT III antibody into contact, followed by a conventional visualization step.

Isolation of the spleen cells and cell hybridization are then performed according to a known method; reference may be made, in particular, to the paper in J. Immunol, Methods, (1980), 35, pp. 1–21, "Production of monoclonal antibodies: strategy and tactics", or to publications describing the preparation of anti-AT III antibodies, and for example to Biochem. Biophys. Acta, (1988), 952, pp. 37–47.

The identification of the hybridomas secreting monoclonal antibodies which display one or other of the affinities characteristic of the different types of antibodies according to the invention may be carried out using an apparatus enabling the intensity of the immunological reactions to be determined, such as the apparatuses mentioned above.

It is also possible, when an antibody corresponding to the invention has been isolated previously, to look for a complementary antibody by employing a sandwich type immunoassay with native, activated or denatured AT III, according to the case, as antigens.

Complementary antibodies are understood to mean an antibody of the invention which recognizes activated AT III better than native AT III and an antibody of the invention which recognizes denatured AT III and hardly recognizes native and activated AT III, so that, when employed in a sandwich type immunometric assay method for example, they preferentially recognize activated AT III in solution, given that it is always in the presence of native AT III.

In effect, it has been demonstrated that the complementary antibody (complementary to the antibody of the invention which recognizes activated AT better than native AT) recognizes denatured AT III and hardly recognizes native and activated AT III. This enables antibodies which are useful to the invention to be selected. In effect, this specificity corresponds to the capacity to recognize soluble AT complexed with an antibody of the invention. More precisely, the attachment of AT III to the antibody specific for the activated form promotes the appearance of an epitope which proves also and exclusively to be present on denatured AT III and not on native AT III in solution.

The antibody DSM ACC 2167 can, in particular, be used as known antibody in order to find a complementary antibody; in the case where it is immobilized, after its reaction with AT III or activated AT III in solution and then the monoclonal antibody under study, visualization may be carried out with a labelled anti-mouse IgG antibody (with the proviso that the immobilized antibody DSM ACC 2167 is in Fab or F(ab')$_2$ form and that the anti-mouse IgG conjugate specifically recognizes the Fc portion of the antibody under study); if the monoclonal antibody under study is the component which is immobilized, in particular by adsorption or via an anti-mouse IgG antibody, after its reaction with AT III or activated AT III in solution, visualization may be performed with the labelled antibody DSM ACC 2167. Methods of the same type may be employed to find antibodies similar to the antibody DSM ACC 2167, using a complementary known antibody.

In the case where the selection of the hybridomas is carried out with an apparatus for studying the intensity of immunological reactions, such as the BIACORE® apparatus, to identify a monoclonal antibody recognizing activated AT III in solution better than native AT III, the antibody under study will be bound to the biosensor, and either a solution of activated AT III or a solution of native AT III will be passed through the cell.

To identify a monoclonal antibody that recognizes denatured AT III while hardly recognizing native or activated AT III, the antibody will be bound and a solution of native AT III, then of activated AT III and lastly of AT III denatured by the action of guanidine will be passed through successively.

This type of study is lengthy and expensive, and it is preferable to preselect the hybridomas likely to be suitable by using an immunoassay method.

To select the antibodies that recognize activated AT III better than native AT III, a solid-phase sandwich type immunometric assay may be carried out.

For example, the antibodies in the supernatant under study will be immobilized by adsorption on a surface, or preferably via an anti-mouse immunoglobulin antibody, and then incubated with a solution of AT III containing or not containing the oligosaccharide and, after washing, with a labelled anti-AT III antibody, before performing the visualization in a conventional manner.

To select the antibodies that recognize denatured AT III, the AT III will be adsorbed on a surface optionally in the presence of the oligosaccharide before incubation with the antibody under study; visualization will be performed with a labelled anti-mouse immunoglobulin antibody.

The selected antibodies corresponding to the invention may be produced in sufficient amounts in ascites, on mice pretreated with pristane; they may then be purified by chromatography on a column to which protein A has been bound, for example on a Sepharose® column. These techniques are well known and are described for antibodies directed against AT III in Hybridoma, (1991), 10, pp. 633–640.

In all the immunoassays, the mole ratios of the activating oligosaccharide and of AT III may be greater than those which can be found in vivo; nevertheless, the concentration of activator used will preferably not be multiplied by more than 10 relative to its usual concentration in vivo, while the concentration of AT III will remain close to its physiological concentration, between 1 $\mu$M and 4 $\mu$M approximately.

According to another aspect, the invention relates to a method for the in vitro determination of AT III activated by a sulphated glycosaminoglycan, or a sulphated oligosaccharide which is a biological analogue of heparin, which consists in performing an immunoassay of the so-called sandwich or two-site type, using a monoclonal antibody which recognizes AT III activated by a sulphated glycosaminoglycan, or by one of the sulphated oligosaccharides having an activity with respect to AT III similar to that of heparin, better than AT III in solution, and a monoclonal antibody which hardly recognizes native AT III and activated AT III but recognizes AT III denatured by the action of guanidine or one of its salts, or by adsorption.

The monoclonal antibodies suitable for these assays may be obtained with animals immunized against AT III in the presence of a sulphated glycosaminoglycan which may be different from the one present in the sample to be determined, and the immunization is preferably carried out, in general, with a sulphated oligosaccharide which complexes AT III and has antithrombotic activity, such as the pentasaccharide A mentioned above. Nevertheless, in particular because, after treatment of a subject with any one of the activating glycosaminoglycans, only a small proportion of the AT III is in activated form, it is necessary to plot the calibration curve, enabling the amount of AT III in activated form to be determined in a biological fluid, with solutions of AT III activated by the same glycosaminoglycan as the known one which it is desired to study.

Using the monoclonal antibodies according to the invention, it is possible to perform sandwich (or concentration-saturation) type immunoassays. According to these types of assay, a first antibody is immobilized on a solid surface. The solution to be assayed is then deposited on the immobilized antibody. The latter immuno-captures the antigen which, in the present case, is human antithrombin III. A second antibody coupled to a label, such as $^{125}$I, enzyme or biotin, is then incubated. After washing, the immobilized first antibody-antigen-labelled second antibody complex is visualized.

The assay is termed "one-stage" when the labelled second antibody is incubated simultaneously with the sample containing the antigen to be assayed.

The assay is termed "two-stage" when the incubation of the sample containing the antigen to be assayed with one of the antibodies is performed first, and then, after an optional wash, the second antibody is introduced and incubation is performed again.

According to a variant, the immunoassay is performed in one stage, that is to say the solution under study is incubated simultaneously with both antibodies, before separating the unreacted labelling antibody and performing the visualization by a suitable technique.

More especially, according to this method, the antibody which recognizes denatured AT III is immobilized beforehand on a solid support, before being brought into contact with a solution containing AT III and a solution containing a second antibody which recognizes AT III activated by a sulphated glycosaminoglycan, or one of the sulphated oligosaccharides having an activity with respect to AT III similar to that of heparin, better than AT III in solution, the said second antibody being conjugated to an enzyme label such as peroxidase.

A preferred method of determination consists in performing a one-stage sandwich method, with the immobilized antibody DSM ACC 2167 and a complementary antibody coupled to an enzyme such as peroxidase, either directly or via the biotin/avidin system, in a manner known per se; visualization is performed as usual by the action of the enzyme on a chromogenic substrate.

According to a preferred variant of the invention, the immunoassay is performed in two stages. In this case, the sample to be assayed will first be incubated with an antibody immobilized on a solid surface. After incubation and washing, a second antibody coupled to an enzyme will enable the immune complex, immobilized antibody-antigen-labelled second antibody, which will be formed after a second incubation, to be demonstrated.

An especially preferred method of determination consists in performing a two-stage sandwich test. According to this method, an antibody complementary to the antibody DSM ACC 2167 is immobilized on a solid surface, for example in a well of a microplate. The solution to be assayed is added to the well. After incubation and washing, the antibody DSM ACC 2167 coupled to an enzyme such as peroxidase, either directly or via the biotin/avidin system, is added. After a second incubation and washing, visualization is performed by the action of the enzyme on a chromogenic substrate. It is preferable for the antibody DSM ACC 2167 to be coupled directly to an enzyme.

It will be preferable to use as diluent solution phosphate buffered saline or a trishydroxymethylaminomethane (Tris) -based buffer which is isotonic and lacks free calcium, in view of the phenomena of association between AT III and glycosaminoglycans. The solution will be made isotonic, for example, by adding NaCl, in general at a concentration in the region of 0.15M; to remove calcium ions, they may be complexed by adding a known sequestering agent such as ethylenediaminetetraacetic acid (EDTA).

However, when two-stage sandwich tests are carried out, it is also possible to use buffers containing $CaCl_2$.

The immunoassay according to the invention makes possible not only the evaluation of the anticoagulant activity due to antithrombin III activated by exogenous sulphated glycosaminoglycans during a prophylactic or therapeutic treatment, but also that of the anticoagulant activity linked to AT III activated by the endogenous glycosaminoglycans.

The immunological method according to the invention hence finds application also in the evaluation of the risks of cardiovascular disease.

In what follows, examples are described of two variants of the method for the determination of AT III in the plasma of subjects treated with a low molecular weight heparin, preceded by a description of the obtaining of monoclonal antibodies according to the invention.

EXAMPLE 1

Obtaining of monoclonal antibodies

1. Immunization of animals

A daily dose of 20 µg per mouse of the pentasaccharide A is administered intraperitoneally for 5 days to four balb/c mice, and 20 µg of human AT III in the presence of Freund's complete adjuvant are also administered subcutaneously on the second day. A booster according to the same protocol is performed one month later, and after a few days the mouse is selected whose serum gives the strongest immunological response with respect to AT III in the presence or absence of the pentasaccharide A.

Selection of the mice is performed by a conventional ELISA type immunoassay in wells to the walls of which of which an anti-mouse IgG antibody has been bound. The test serum is incubated therein and then, after washing, a 1 µg/ml solution of human AT III in phosphate buffered saline (PBS) containing 0.1% of Tween® 20, or the same solution containing, in addition, 1 µg/ml of the pentasaccharide A, is introduced.

After incubation for two hours at room temperature followed by a wash, an aqueous solution containing 0.5 µg/ml of anti-AT III polyclonal antibody coupled directly to peroxidase is introduced and, after 30 minutes of incubation, visualization is carried out in a conventional manner.

Selection of the mice may also be performed in the following manner with adsorbed AT III: 100 µl of 10 µg/ml solution of AT III in PBS buffer containing or not containing 10 µg/ml of pentasaccharide A are incubated overnight at +4° C. or 1 hour at 37° C. in the wells of a suitable microtitration plate in order to effect the adsorption of the AT III on the walls in a known manner; after washing of the wells, 100 µl of serum diluted from 1000 to 10,000 times in phosphate buffer are incubated therein and, after washing, an anti-murine IgG antibody conjugated to an enzyme is introduced and then visualized in the usual manner. The mouse whose serum had the best titre was chosen.

2. Lymphocyte hybridization

Fusion is carried out by the action of polyethylene glycol with mouse myeloma cells, of the line P3-X63-Ag-8653 described in J. Immunol. Methods, (1979), 123, pp. 1548–1550, and spleen cells of the selected mouse. The hybridomas are cultured on the usual RPMI-based media marketed by Gibco, containing foetal calf serum, hypoxanthine, thymidine and aminopterin, and then selected by applying the same methods as for the characterization of the mouse sera. The selected hybridomas are then cloned by limiting dilution from a dilution to 50 cells per ml, on the basis of 100 µl per well of a cloning plate.

3. Study of the affinity of the antibodies for AT III and activated AT III

A BIACORE® apparatus is used, the signal from which, expressed in resonance units, is a linear function of the amount of proteins bound to the surface of the biosensor between 1 $pg/mm^2$ and 30 $ng/mm^2$ for proteins of molecular mass between 25,000 and 150,000 approximately. A rabbit anti-mouse immunoglobulin antibody, to which the antibodies under study are immunologically bound from a 100 µg/ml solution in 10 mM phosphate buffer containing 150 mM NaCl and 5 mM EDTA, pH 7.4, is immobilized on the sensitive surface by covalent bonding to the hydrogel which coats it, according to the method recommended by the manufacturer; the signals obtained on passing through the cell normal human plasma diluted with the buffer so as to contain approximately 0.52 µM AT III, and the same diluted plasma containing one of the sulphated glycosaminoglycans at a concentration of 52 µM, are noted.

Table I gives the measurements recorded for 12 hybridoma supernatants with a low molecular weight heparin, Fraxiparin® (INN nadroparin calcium), classified in four groups; the group 1 antibodies hardly recognize native or activated AT III in solution; those of group 2 recognize native and activated AT III in the same manner and do not correspond to the invention; the group 3 antibodies recognize native AT III better than activated AT III and do not correspond to the invention, in contrast the group 4 antibodies are better at recognizing AT III activated by low molecular weight heparin, and may be used to perform the method of the invention for the determination of activated AT III; their complementary antibodies will be selected from those of group 1.

TABLE I

| ANTIBODY | SIGNAL | | GROUP |
|---|---|---|---|
| | AT III | activated AT III* | |
| SR at 01 | 17 | 23 | 1 |
| SR at 02 | 67 | 60 | 1 |
| SR at 03 | 70 | 56 | 1 |
| SR at 04 | 115 | 120 | 2 |
| SR at 05 | 548 | 336 | 3 |

TABLE I-continued

| ANTIBODY | SIGNAL | | GROUP |
| --- | --- | --- | --- |
| | AT III | activated AT III* | |
| SR at 06 | 465 | 260 | 3 |
| SR at 07 | 404 | 123 | 3 |
| SR at 08 | 367 | 207 | 3 |
| SR at 09 | 395 | 121 | 3 |
| SR at 10 | 382 | 123 | 3 |
| SR at 11 | 208 | 297 | 4 |
| SR at 12 | 346 | 421 | 4 |

*activator/AT III mole ratio = 100

The signals obtained with the antibodies SR at 11 and SR at 12 for AT III in the presence of different sulphated glycosaminoglycans were also measured under the same conditions; the results appear in Table II:

TABLE II

| ACTIVATOR | SIGNAL (activated AT III*) Ab SR at 11 | SIGNAL (AT III) Ab SR at 12 |
| --- | --- | --- |
| Heparin | 236 | 121 |
| Fraxiparin | 160 | 121 |
| Pentasaccharide A | 29 | 86 |

*activator/AT III mole ratio = 10

It is seen that it would be preferable not to use the antibody SR at 11 for a study of the in vivo activation of AT III by the pentasaccharide A, while it would be suitable in the case of an activation by heparin. When it is desired to apply the method according to the invention in the case of an activator of unspecified nature, the antibody SR at 12 may be selected.

The association constants of the groups 3 and 4 monoclonal antibodies (SR at 07, SR at 11 and SR at 12) with antithrombin III were also evaluated in the presence and absence of a low molecular weight heparin (LMWH), and in particular nadroparin calcium.

As demonstrated by the results in Table III, the association constant of the two group 4 monoclonal antibodies increases in the presence of a low molecular weight heparin, in contrast to that of the group 3 antibody SR at 07.

For the tests, a BIACORE® apparatus was used, and the tests were performed under the conditions described above. It should be noted that the tests in the presence of nadroparin calcium were carried out maintaining the low molecular weight heparin/AT III mole ratio constant. The plasma AT III concentration varied from 0.520 $\mu$M to 0.00325 $\mu$M.

4. Selection of an antibody complementary to those of group 4

This antibody is looked for among those which give weak signals in the BIACORE® apparatus and recognize denatured AT III in solution.

Purified commercial AT III is denatured by treatment with guanidine hydrochloride: a 10 mM phosphate buffer solution containing 50 $\mu$g/ml of AT III, 150 mM NaCl and 0.9M guanidine at pH 7.4 is left to incubate for 18 hours at +4° C.; the solution obtained is dialysed against 10 mM phosphate buffer containing 150 mM NaCl, pH 7.4, to obtain a 500 $\mu$g/ml solution of denatured AT III.

The selection is performed using the results of a solid-phase immunoassay: the test antibodies are adsorbed in the wells of a microplate by contact of a 10 $\mu$g/ml solution of antibody in phosphate buffered saline for 18 hours at +4° C.; the wells are washed and 100 $\mu$l of a 10 $\mu$g/ml solution of native or denatured AT III in 10 mM phosphate buffer containing 150 mM NaCl and 5 mM EDTA at pH 7.4 are introduced; after one hour of incubation at room temperature and washing, 0.05 $\mu$g of an anti-AT III polyclonal antibody coupled to peroxidase, in solution at a concentration of 0.5 $\mu$g/ml, is placed in the wells. After one hour of incubation and washes, visualization is carried out by adding $H_2O_2$ and ortho-phenylenediamine, followed by stopping of the reaction by adding $H_2SO_4$.

The ratio of the absorptions of light at about 490 nm for the test with native AT III relative to that with denatured AT III is less than 0.1 for the antibody SR at 02, whereas it is greater than 0.4 for the antibodies SR at 01 and SR at 03; hence these latter do not form part of the invention. The antibody SR at 02 was deposited at the DSM collection under ACC 2167.

EXAMPLE 2

Obtaining a calibration curve for the method for the immunodetermination of AT III activated by a low molecular weight heparin—One-stage assay 100 $\mu$l of a 10 $\mu$g/ml solution of the antibody SR at 02 in solution in 10 mM phosphate buffer, pH 7.4, containing 150 mM NaCl and 5 mM EDTA are introduced into the wells of a microtitration plate. After incubation for 18 hours at +4° C. and washes with the buffer solution, 50 $\mu$l of a 0.5 mg/ml solution diluted to 1/40,000 of the antibody SR at 12 conjugated to peroxidase and 50 $\mu$l of a reference solution containing normal plasma and low molecular weight heparin (Fraxiparin) are introduced, and the mixture is left to incubate for two hours at room temperature before washing and performing the visualization by adding a chromogenic substrate for the enzyme, for example orthophenylenediamine and $H_2O_2$. Light absorption is determined at 490 nm or 492 nm after adding 4N $H_2SO_4$ to the wells.

TABLE III

| | | Plasma alone | | | Plasma with LMWH | | |
| --- | --- | --- | --- | --- | --- | --- | --- |
| Group | Antibody | kon (1/Ms) | koff (1/s) | Ka (1M) | kon (1/Ms) | koff (1/s) | Ka (1M) |
| 3 | SR at 07 | 3.6E+05 | 5.4E−04 | 6.6E+08 | 2.2E+05 | 9.6E−04 | 2.3E+08 |
| 4 | SR at 11 | 2.0E+05 | 3.7E−03 | 5.3E+07 | 5.0E+05 | 1.6E−03 | 3.2E+08 |
| 4 | SR at 12 | 2.7E+04 | 4.7E−04 | 5.8E+07 | 3.5E+05 | 5.4E−04 | 6.4E+08 | kon (1/Ms) = rate of association constant
koff (1/s) = rate of dissociation constant
Ka (1/M) = affinity constant The reference solution is obtained by diluting 10-fold in phosphate buffer the solution resulting from the incubation (for example for 2 hours) at room temperature of a mixture of 800 μl of the above phosphate buffer with 100 μl of normal plasma whose AT III concentration is estimated at around 2.6 μM, and 100 μl of a solution of Fraxiparin containing, as appropriate, from 0.26 μM to 260 μM activator.

The antibody is conjugated to peroxidase according to a well-known method, which consists in reacting the antibody and peroxidase activated by treatment with sodium periodate before stabilizing the compound obtained by treatment with sodium borohydride (Nakane's method).

Figure 1:
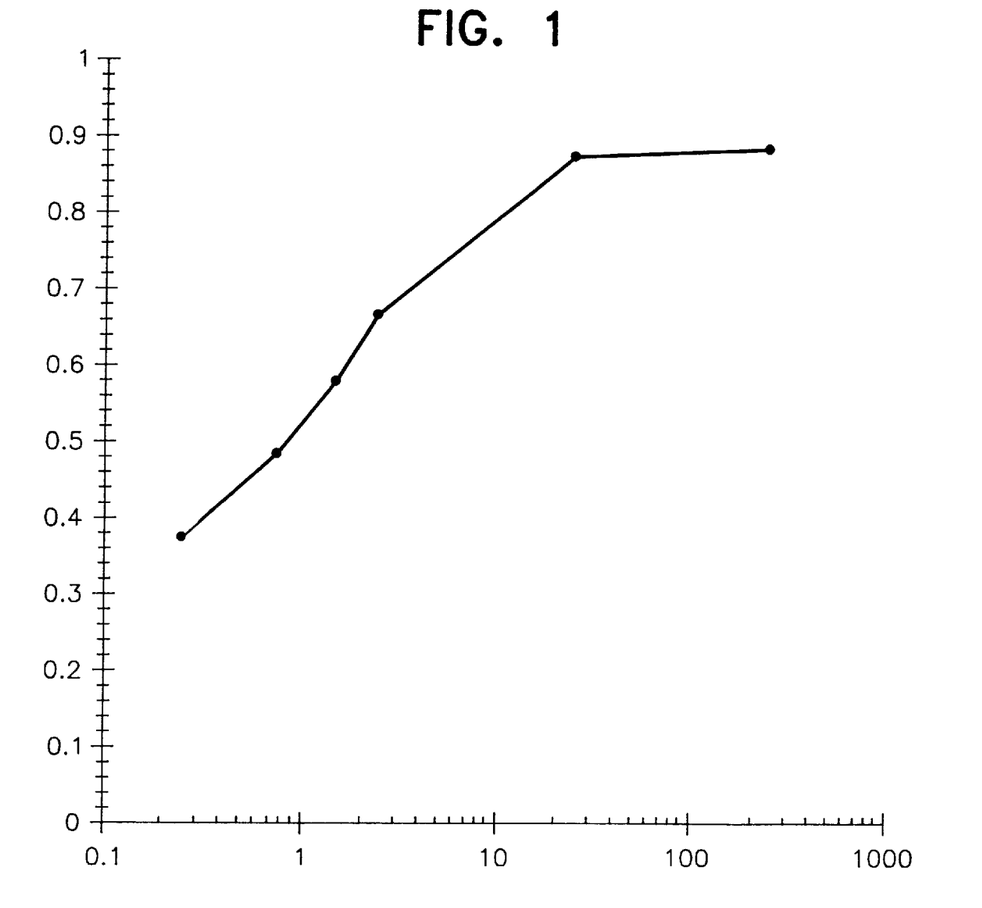
FIG. 1 is a graph of absorbance vs. activator concentration.

FIG. 1 gives, in semilogarithmic coordinates, the absorbance at 490 nm as ordinates and the concentrations of the activator, expressed in μM Fraxiparin in the 100 μl introduced into the medium, as abscissae.

EXAMPLE 3

Immunoassay in the plasma of a subject treated with Fraxiparin—One-stage assay 35,000 units of Fraxiparin are administered subcutaneously to healthy volunteers after drawing a first blood sample for the purpose of determining their plasma concentration of native AT III; 1-ml blood samples are thereafter drawn every ½ hour for the first 5 hours and then after 6, 8, 12, 18, 24, 30, 36 and 48 hours. On each sample, the plasma concentration of activated AT III is determined by the method according to the invention described in Example 2.

Figure 2:
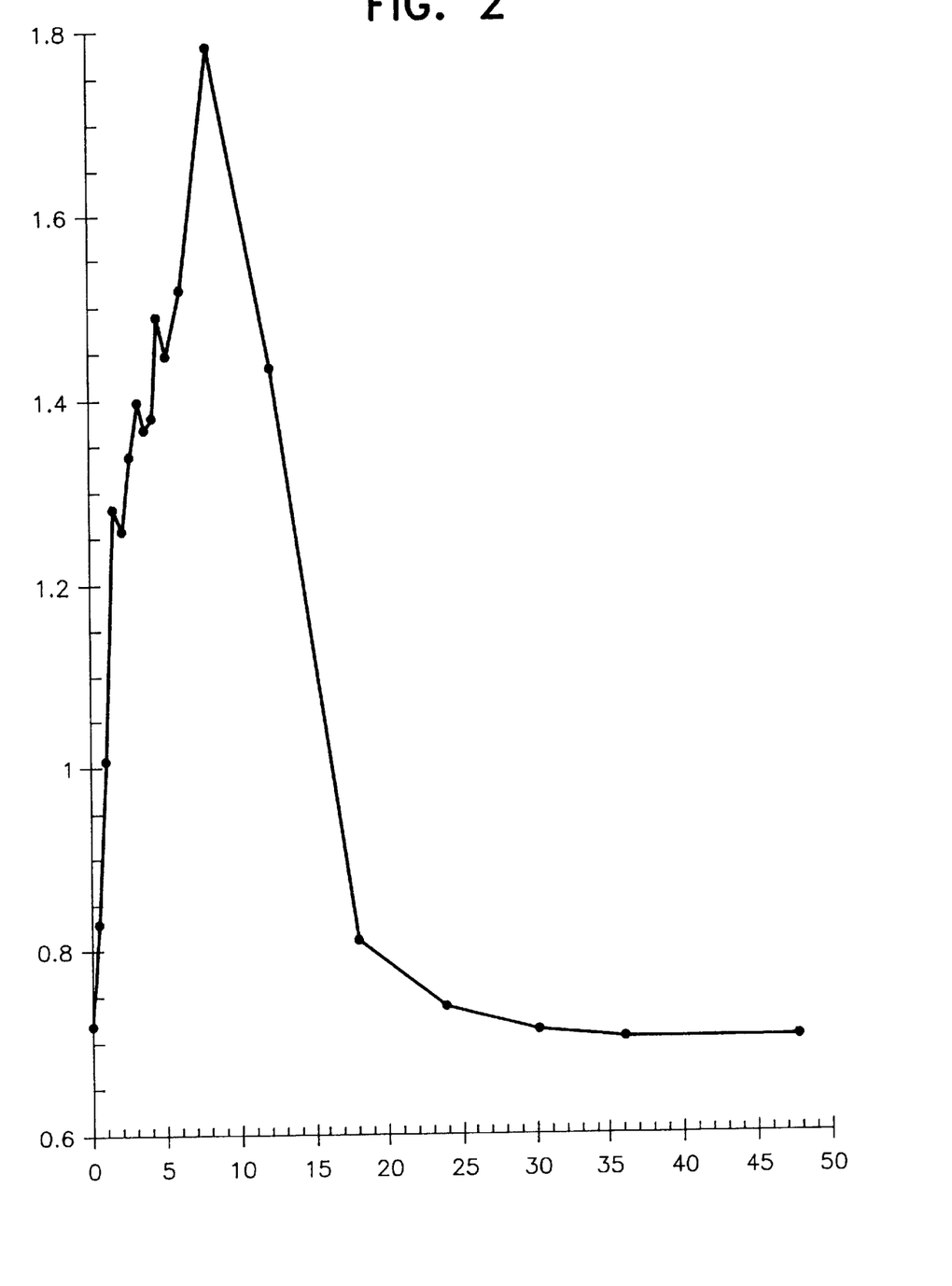
FIG. 2 is a graph of absorbance vs. time.

Figure No. 2 shows the absorbance measured in terms of time.

EXAMPLE 4

Immunoassay of AT III activated in vitro before and after treatment with heparinase—One-stage assay A 2.7 μM solution of purified AT III in 10 mM phosphate buffer containing 150 mM NaCl and 5 mM EDTA, pH 7.4, is incubated (for example for two hours) at room temperature, as is the same solution containing heparin at the same concentration as AT III. These solutions are then diluted 100-fold in the same buffer and incubated for one hour at room temperature with heparinase; this reaction is performed by introducing 0.5 ml of diluted solution into a vial of 1000 IU of Hepzyme Dade heparinase marketed by Baxter under the reference B4240-10 (heparinase EC 4.2.2.7.).

The immunoassay is performed according to the method of the invention already described in Example 2, with the immobilized antibody SR at 02 and the antibody SR at 12 coupled to biotin by the action of N-hydroxysuccinimidobiotin, at a concentration of 1 μg/ml. Visualization is then performed by adding 50 μl of a solution of avidin coupled to peroxidase, marketed by Pierce under the reference 29994 and diluted 500-fold in the phosphate buffer; after 15 minutes of incubation, the wells of the plate are washed 4 times and the residual peroxidase activity is measured as in Example 2. The optical density of the two samples without heparin is very low, in the region of 0.1, while the sample containing heparin has an optical density in the region of 2 which, after treatment with heparinase, then becomes only 0.5.

EXAMPLE 5

Obtaining a calibration curve for the method for the immunodetermination of AT III activated by an unfractionated heparin—Two-stage assay 100 μl of a 10 μg/ml solution of antibody SR at 12 in solution in 10 mM phosphate buffer solution (pH 7.4) containing 150 mM NaCl and 5 mM EDTA are introduced into the wells of a microtitration plate. After incubation for 18 hours at +4° C. and washes with the buffer solution, 100 μl of plasma overloaded or not overloaded with unfractionated heparin and diluted beforehand to ¹⁄₁₀₀ in the phosphate buffer solution are introduced.

The plate is incubated for 45 minutes at room temperature and washed with the phosphate buffer solution. 100 μl of a 0.5 mg/ml solution diluted to ¹⁄₂₅₀₀ of the antibody SR at 02 conjugated to peroxidase are then added. For the dilution, the same phosphate buffer solution described above is used. The plate is incubated for 45 minutes and washed with the same buffer solution.

Visualization is performed by adding a chromogenic substrate for the enzyme, for example by adding 100 μl of a solution of ortho-phenylenediamine and $H_2O_2$. After 15 minutes at room temperature, the reaction is stopped by adding 50 μl of 4N $H_2SO_4$ and the absorption is read at 492 nm.

The reference solution is obtained by diluting 100 μl of normal plasma whose AT III concentration is in the region of 2.6 μM to ¹⁄₁₀₀ with phosphate buffer.

Figure 3:
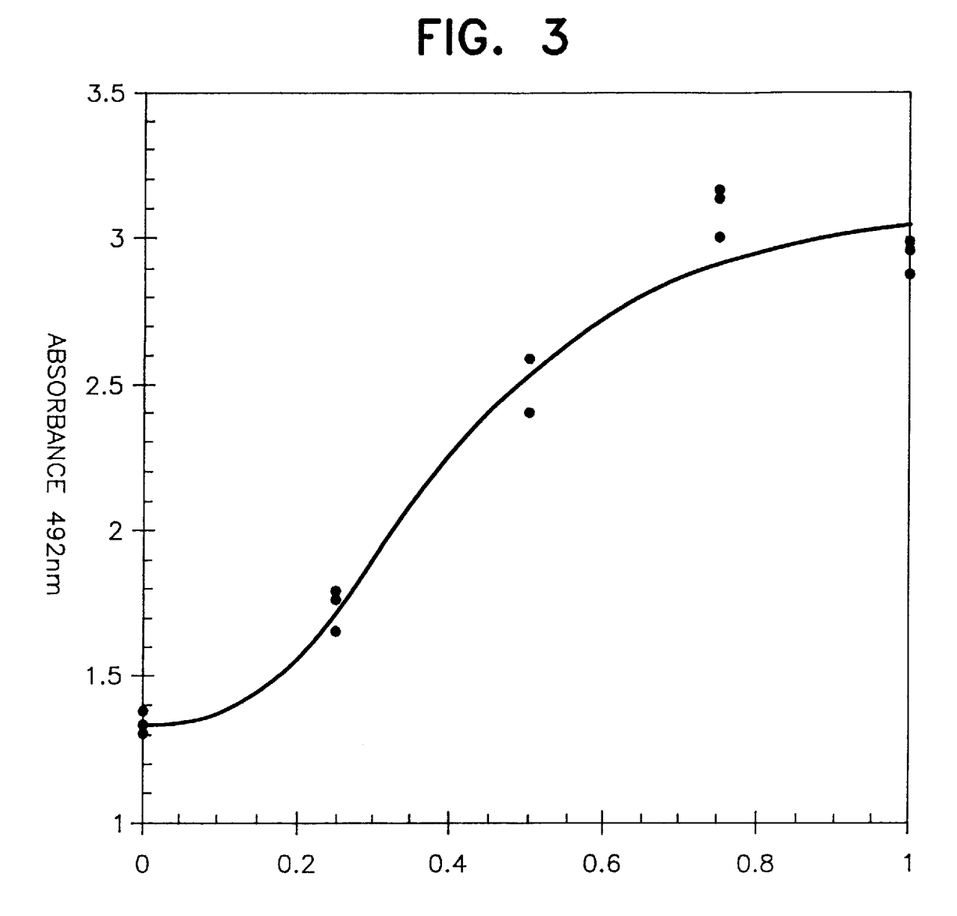
FIG. 3 depicts a graph of absorbance vs. heparin concentration.

For the calibration series, the plasma was overloaded before dilution with increasing amounts of an unfractionated heparin (UFH). The UFH/AT III mole ratios were from 0:1 (reference) to 1:1. FIG. 3 gives the absorbance at 492 nm as ordinates and the concentrations of the activator, expressed in moles of UFH/mole of AT III, as abscissae.

The signal measured with this two-stage assay is perfectly well correlated with the anti-Xa activity evaluated by a biological assay (R=0.980). Comparisons were carried out with plasma originating either from healthy volunteers or from patients treated with the speciality Fraxiparin®.

In these tests, the anti-Xa activity was evaluated by the Rotachrome® technique of Stago.

EXAMPLE 6

Evaluation of the plasma anticoagulant activity after venous occlusion—Implementation of the two-stage assay In order to demonstrate a possible increase in the level of circulating endogenous glycosaminoglycans when there is an endothelial lesion/stimulation like that produced before and after venous occlusion, a study was carried out in 6 healthy volunteers and 17 patients suffering from more or less serious cardiovascular pathologies.

The test of stimulation of the vascular endothelium is, for example, the venostasis test. This test consists in placing a cuff adjusted to 100 mm of mercury on a patient's limb (generally an arm, more rarely a leg). After a wait of 10 minutes, the blood is recovered. A sample before venostasis is also drawn.

This test induces a haemoconcentration (determined by the haematocrit) as well as some degree of damage to the vascular endothelium, causing the liberation of substances present in or at the surface of the endothelial cells. This test is normally used to assess the fibrinolytic activity of these cells. An injection of desmopressin causes a pharmacological stimulation of the endothelium with effects similar to a venostasis.

Test 1

In order to avoid all interference due to plasma proteins, the immunoassay was performed with the plasma diluted to ¹⁄₁₀₀₀ in the following manner:

Plasma of 6 healthy volunteers and 17 patients is drawn onto citrate and stored at −20° C. until the time of assay.

The antibody SR at 12 is adsorbed on microplates according to the protocol described in Example 5. 100 μl of plasma diluted to ¹⁄₁₀₀₀ in 10 mM phosphate buffer (pH 7.4) containing 150 mM NaCl and 5 mM EDTA are then introduced into the microplates containing the antibody SR at 12. The plates are incubated for 45 minutes at room temperature and washed with the phosphate buffer solution mentioned above. 100 µl of a solution of the antibody SR at 02 conjugated to peroxidase (diluted to 1/500 in the phosphate buffer solution) are then added.

After incubation for 45 minutes at room temperature, the microplates are washed with the same buffer solution.

The residual peroxidase activity is visualized by adding a chromogenic substrate, and in particular 100 µl of a solution of ortho-phenylenediamine and $H_2O_2$. After 15 minutes, the reaction is stopped by adding 50 µl of 4N $H_2SO_4$ and the absorbance is read at 492 nm. The signal measured in the samples drawn after venostasis is corrected by taking account of the haemoconcentration.

The first results obtained in this direct evaluation did not enable a significant difference to be demonstrated between the patients and the healthy volunteers.

On the other hand, it was demonstrated that the difference in the signals (Δ) which is measured before and after venostasis, patient by patient, according to the following formula:

Δ = (corrected signal* measured after venostasis) −

(signal measured before venostasis) * corrected signal =

(signal read) × $\frac{\text{haematocrit before venostasis}}{\text{haemotacrit after venostasis}}$ is significantly smaller in patients having a cardiovascular pathology than in healthy volunteers.

Under the same experimental conditions and with other markers of haemostasis [such as total antithrombin (total AT), prothrombin fragments 1+2 (F1+2) or thrombin-antithrombin complex (T-AT complex)], there is no significant difference between healthy volunteers and patients. The immunoassay method according to the invention constitutes a very efficacious tool for detecting the risks of cardiovascular disease.

Test 2

To confirm these results and demonstrate that the increase in the signal measured with the plasma drawn after venostasis is caused by a circulating endogenous glycosaminoglycan, the following test was carried out. The plasmas (before and after venostasis) of three healthy volunteers were assayed before and after heparinase treatment according to the following protocol:

The plasmas were diluted to 1/250 in a buffer solution (pH 7.4) containing 10 mM Tris, 150 mM NaCl, 5 mM $CaCl_2$ and 5 µg/ml hirudin, and 500 µl of the diluted plasma were incubated in a vial of Hepzyme for 2 hours at room temperature. The plasmas were then diluted to ¼ in 10 mM phosphate buffer solution (pH 7.4) containing 150 mM NaCl and 5 mM EDTA.

The immunoassay is then performed as described in test 1 above.

Figure 4:
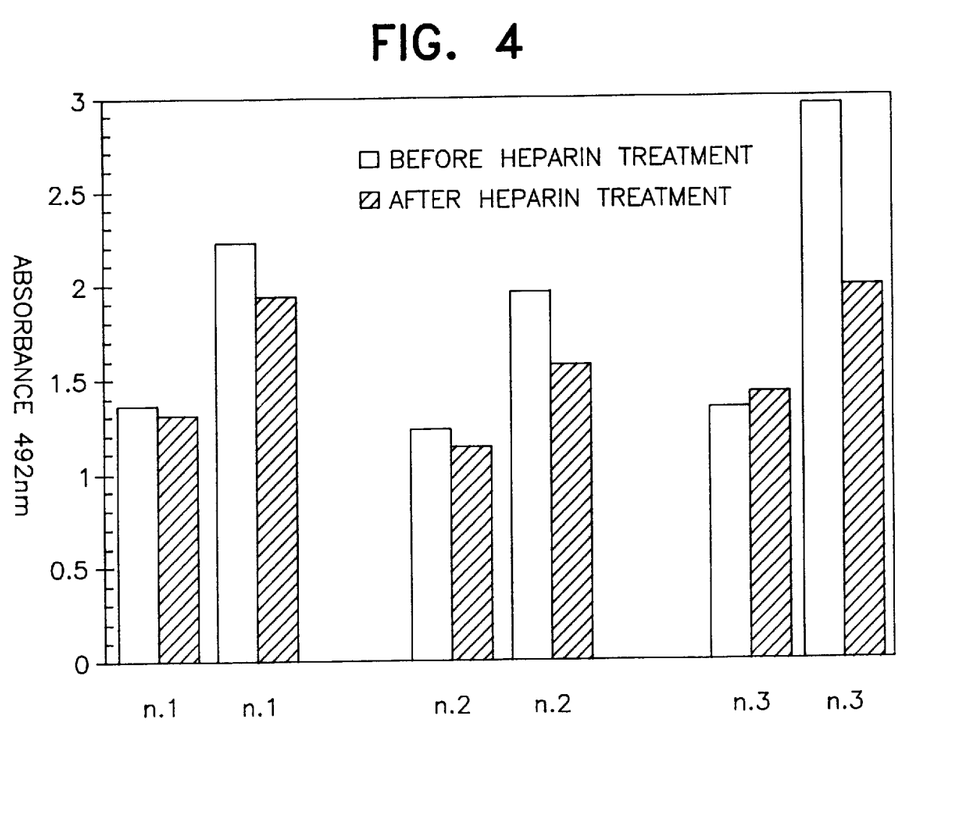
FIG. 4 depicts the results of immunoassays before and after treatment.

The results obtained, shown in FIG. 4, demonstrate that heparinase treatment of plasmas drawn before venostasis does not significantly modify the signal. On the other hand, heparinase treatment of plasmas drawn after venostasis significantly decreases the signal.

The signal thus decreased is, however, greater than that from plasma drawn before venostasis.

The results of tests 1 and 2 suggest that an endothelial abnormality in subjects having repeated venous thromboses might be the cause of a predisposition to the risk of thrombosis.

It would appear that, in a normal individual, the endothelial cells, following vascular damage, liberate an anticoagulant activity into the bloodstream. This anticoagulant activity, which is considered to be linked to activated AT III associated with endogenous glycosaminoglycans (or heparin-like substances), would decrease in patients having a cardiovascular pathology. This decrease is considered to be due to the liberation (smaller in patients) of endogenous glycosaminoglycans.

The results in FIG. 4 also suggest that the substance liberated into the blood during venostasis would probably be a glycosaminoglycan of the "heparin" type, since the measured signal increases very significantly after venostasis and is partially decreased by heparinase treatment.

We claim:

1. Monoclonal antibody that binds denatured AT III while not substantially binding AT III and AT III activated by a sulphated glycosaminoglycan whose effect in vivo on AT III is analogous to that of heparin.

2. Monoclonal antibody according to claim 1, secreted by the hybridoma deposited at the DSM collection under the No. ACC 2167.

3. Monoclonal antibody that specifically binds AT III activated by a sulphated glycosaminoglycan, and which promotes the appearance of an epitope on denatured AT III.

4. Monoclonal antibody according to claim 3, characterized in that the sulphated glycosaminoglycan is the pentasaccharide of formula:

5. Method for obtaining a monoclonal antibody according to claim 3, characterized in that animals are immunized with human antithrombin III and a sulphated oligosaccharide whose effect in vivo on AT III is analogous to that of heparin, and in that the hybridomas which secrete antibodies displaying the desired immunological properties are selected.

6. Method according to claim 5, characterized in that the sulphated oligosaccharide is the pentasaccharide of formula:

7. Method according to claim 5, for the isolation of antibodies, characterized in that the selection of suitable hybridomas is performed using an apparatus for measuring immunological affinities.

8. Method according to claim 5, characterized in that the selection is performed with an apparatus which determines the rate of binding of macromolecules to a surface by measuring the reflection of a polarized light ray and employing the phenomenon of surface plasmon resonance.

9. Method according to claim 5, characterized in that a pre selection of the hybridomas secreting antibodies is performed before their cloning by limiting dilution, by an immunoassay with an anti-AT III polyclonal antibody.

10. Method for obtaining a monoclonal antibody which binds AT III activated by a sulfated glycosaminoglycan whose effect in vivo on AT III is analogous to that of heparin, better than native AT III, in solution, comprising immunizing animals with human antithrombin III and a sulfated oligosaccharide whose effect in vivo on AT III is analogous to that of heparin, and selecting hybridomas which secrete antibodies displaying the desired immunological properties, characterized in that the selection of suitable hybridomas is performed by a method according to claim 5 with a known antibody complementary to the one sought.

11. A method that assays activated antithrombin III (AT III), useful for monitoring the effect in vivo of an agent that activates AT III, comprising the steps of contacting AT III with a solution sample containing the agent, wherein the agent is a sulfated glycosaminoglycan or a sulfated oligosaccharide, followed by contacting the sample with i) a first monoclonal antibody that binds AT III activated by the agent, does not find native AT III, and ii) a second monoclonal antibody that binds denatured AT III does not bind either AT III activated by the agent or native AT III.

12. A method according to claim 11, wherein both the first and second antibodies are brought into contact simultaneously with the sample.

13. A method according to claim 11, wherein the first antibody is immobilized on a solid surface and the said second antibody is conjugated with an enzyme label.

14. A method according to claim 11, wherein the sample is contacted with the first antibody and incubated and, after an optional washing step, contacted with the second antibody and incubated.

15. A method according to claim 11, wherein the first antibody is immobilized on a solid surface.

16. A method according to claim 15, wherein the second antibody, is conjugated with an enzyme label.

17. A method according to claim 15, which is carried out in the absence of free calcium ions.

18. A method according to claim 15, wherein the sample includes an agent that complexes free calcium ions.

19. A method according to claim 15, wherein the first antibody is secreted by a hybridoma deposited at the DSM collection under the number ACC 2167.

20. A method according to claim 15, wherein the agent that activates AT III is natural heparin or a heparin having a molecular weight lower than natural heparin.

21. A method according to claim 15, wherein the agent that activates AT III is a pentasaccharide having the formula 22. Method according to claim 15 for detecting the risks of cardiovascular disease.

* * * * *